US00PP20671P3

(12) United States Plant Patent
Skelton

(10) Patent No.: US PP20,671 P3
(45) Date of Patent: Jan. 26, 2010

(54) KIWI PLANT NAMED 'SKELTON A19'
(50) Latin Name: *Actinidia chinesis*
Varietal Denomination: Skelton A19

(75) Inventor: Donald Skelton, Huntly (NZ)

(73) Assignee: Enza Limited, Mt. Wellington (NZ)

( * ) Notice: Subject to any disclaimer, the term of this patent is extended or adjusted under 35 U.S.C. 154(b) by 3 days.

(21) Appl. No.: 12/005,052

(22) Filed: Dec. 21, 2007

(65) Prior Publication Data

US 2008/0184401 P1 Jul. 31, 2008

(51) Int. Cl.
*A01H 5/00* (2006.01)

(52) U.S. Cl. ..... Plt./156

(58) Field of Classification Search ..... Plt./156
See application file for complete search history.

*Primary Examiner*—Annette H Para
(74) *Attorney, Agent, or Firm*—Black Lowe & Graham, PLLC

(57) ABSTRACT

A new and distinct kiwi plant of the species *Actinidia chinensis* is described. The cultivar results from a controlled pollination using a male *A. chinensis* selection 'RY,' and a female *A. chinensis* selection 'A124.' Both named parents ('RY' and 'A124') are unpatented cultivars. The new cultivar is distinguished by its medium fruit size, obovoid fruit shape, greenish-yellow fruit coloring, and its medium to early harvest date in early April.

6 Drawing Sheets

FIELD OF THE INVENTION

Genus and species of plant claimed: *Actinidia chinensis.*

PRIORITY CLAIM

The present application claims priority from New Zealand Plant Variety Rights Application No. KIW026, entitled 'SKELTON A19' filed Dec. 22, 2006, with the Commissioner of Plant Variety Rights in New Zealand, which is herein incorporated by reference.

BACKGROUND OF THE INVENTION

Kiwi plants in cultivation are mainly varieties of *A. deliciosa,* particularly 'Hayward' although some *A. chinensis* and *A. arguta* varieties are grown. *A. deliciosa* and *A. chinensis* are closely related and varieties of both types have large fruit (about 100 g) with hair on the skin. The main varieties in New Zealand are 'Hayward' (*A. deliciosa*) and 'HORT16A' (*A. chinensis*). Fruit are usually cut and eaten with a spoon.

All *Actinidia* species are dioecious, so female varieties have to be interplanted with male pollinizers to ensure fruit production.

*A. chinensis* vines are deciduous and tend to grow vigorously in spring and summer when rapidly-growing shoots can intertwine and tangle if not managed. Vines do best in a mild warm-temperate climate without late spring or early autumn frosts. They produce consistently heavy crops when grown in well-drained fertile soils and given regular irrigation in dry spells.

*A. chinensis* flowers in late September to late October in New Zealand. Harvest of *A. chinensis* fruit occurs from late February to late June in New Zealand depending on the selection and location of plantings.

SUMMARY OF THE INVENTION

The present invention is a new and distinctive kiwifruit variety having a medium sized obovoid fruit shape, a fruit flowering date of early October, with a fruit harvest date of early April. This new variety is designated 'Skelton A19' and is derived from a controlled pollination using a female *A. chinensis* selection 'A124' and a male *A. chinensis* selection RY of unknown parentage.

Neither of the parents are registered with the Plant Variety Rights Office in New Zealand or patented. The parent plants are part of an ongoing breeding program established in New Zealand in 1975.

This new variety was created during the course of a planned plant-breeding program, which was initiated in Waiuku, New Zealand in 1994 and approximately 300 seedlings were raised at Rangiriri, New Zealand. 'Skelton A19' first flowered in October 1998 and fruit were assessed in April 1999. Following fruit assessment, 'Skelton A19' was grafted onto ten *Actinidia deliciosa* seedling rootstocks and onto ten *Actinidia chinensis* seedling rootstocks. The unique characteristics of 'Skelton A19' continued and the asexually reproduced plants were true to type.

The new variety can be asexually reproduced as cuttings or by grafting or budding on to seedling or cutting-grown rootstocks of *A. deliciosa* or *A. chinensis,* or by striking cuttings, or by tissue culture. Trial plantings of grafted plants established in Rangiriri, New Zealand in 1999 have shown that the unique combination of characteristics come true to form, are established, and transmitted through succeeding asexual propagations.

COMPARISON TO CLOSEST VARIETY

Figure 1:
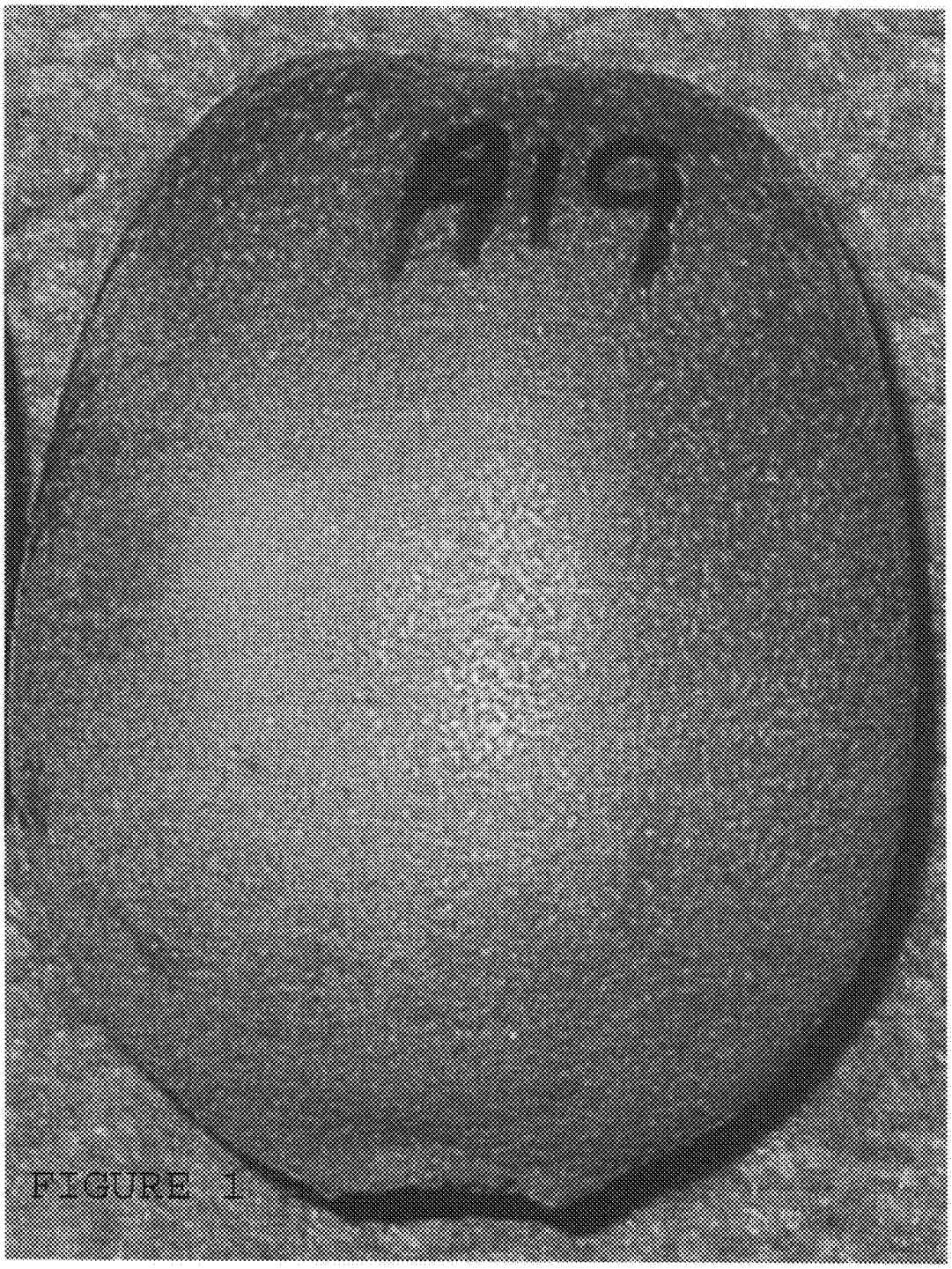
FIG. 1 shows typical fruit of the new variety in the studio.
Figure 2:
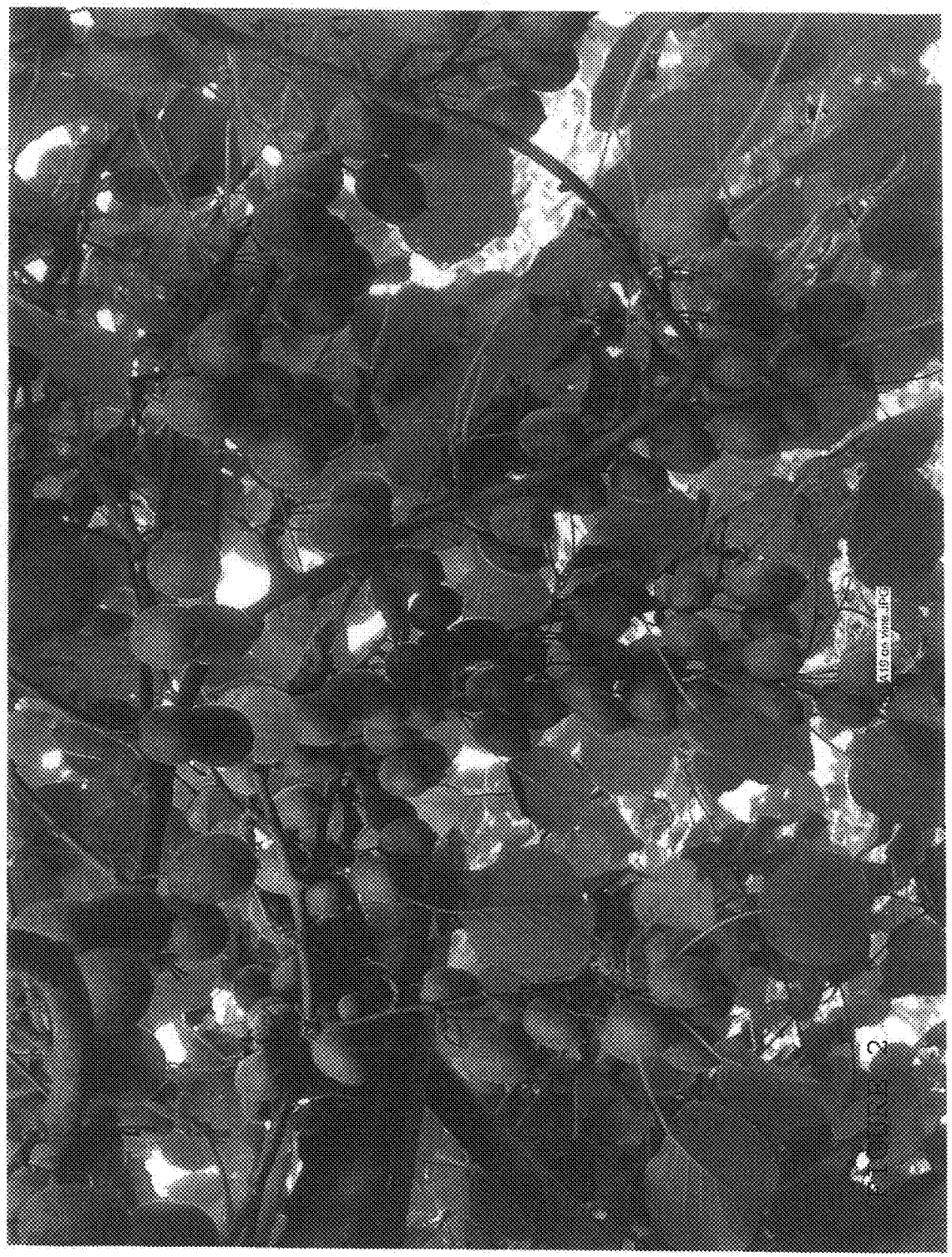
FIG. 2 shows typical fruit of the new variety in the orchard.
Figure 3:
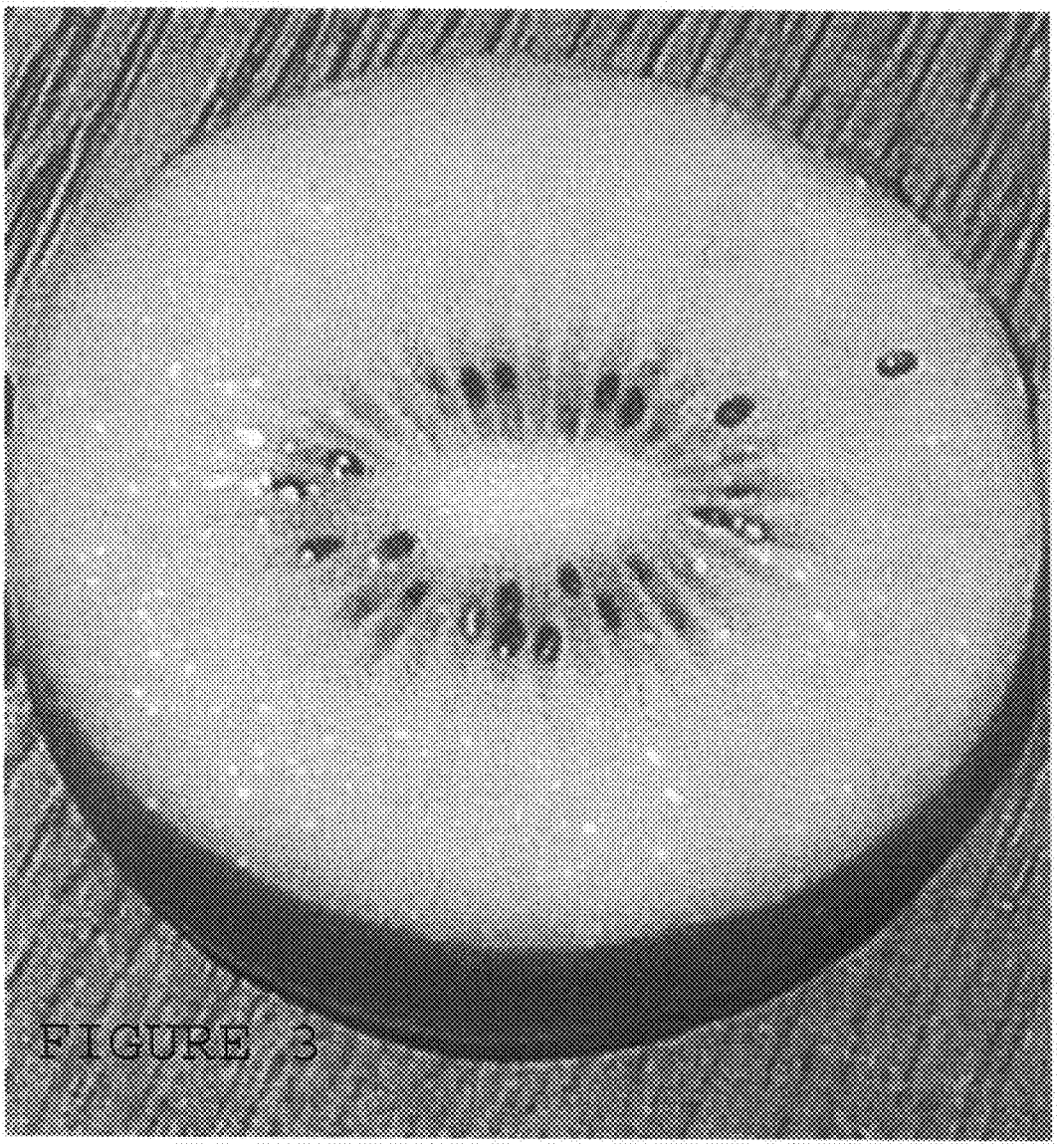
FIG. 3 shows typical fruit of the new variety in cross-section.
Figure 4:
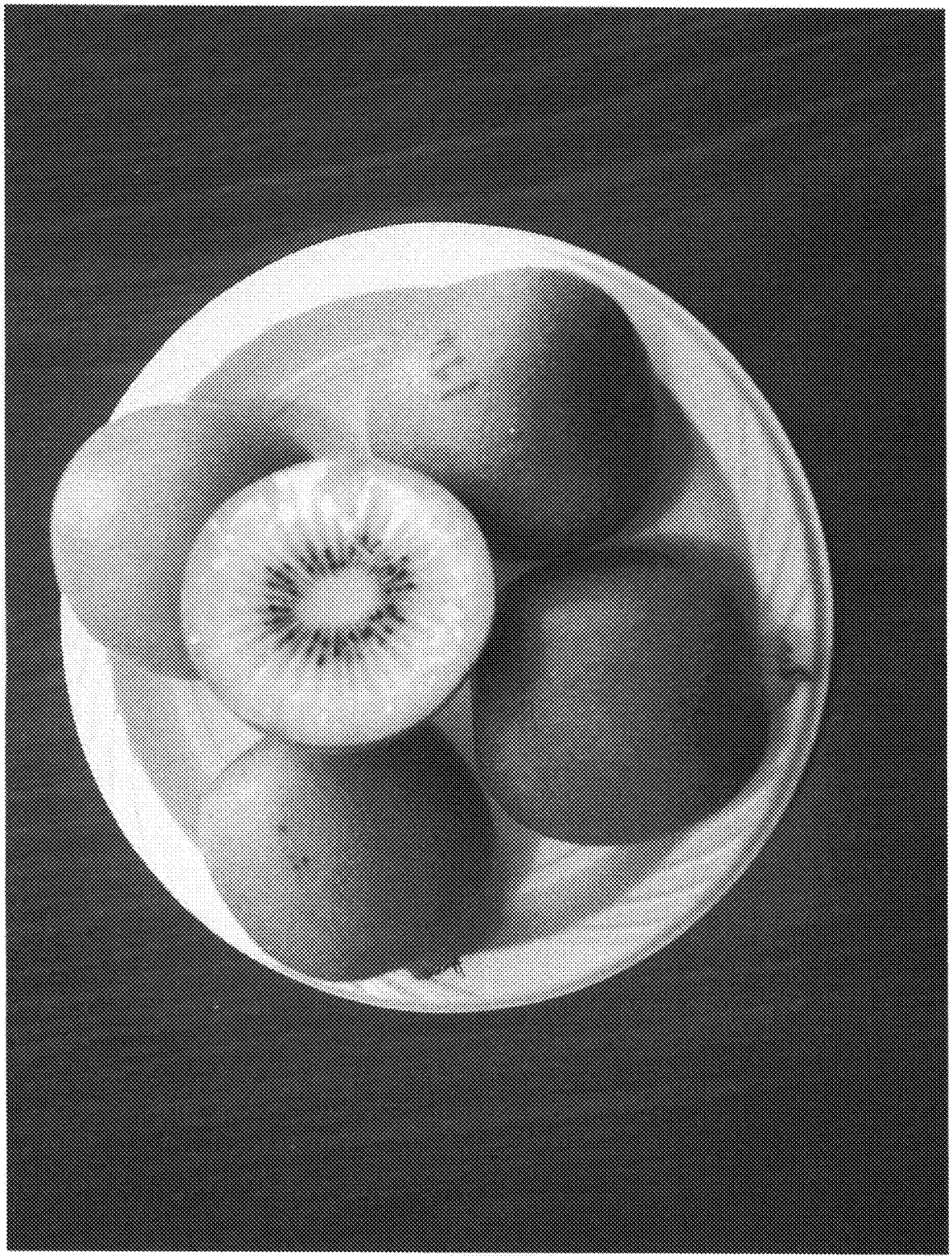
FIG. 4 shows typical fruit of the parent female A124 species in the studio and in cross-section.
Figure 5:
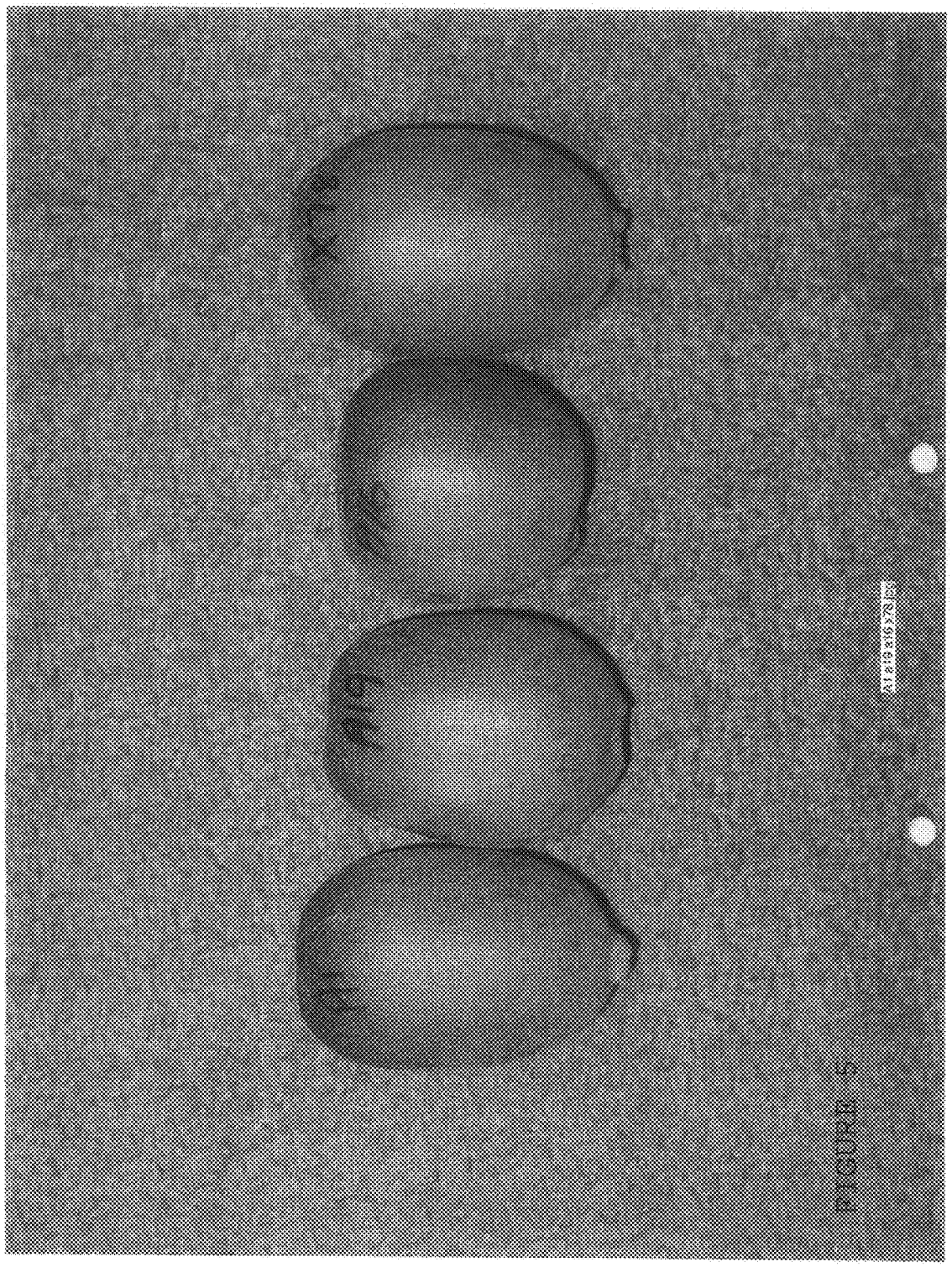
FIG. 5 shows typical fruit of the new variety in the studio compared with other varieties, in order: 'A1'; 'Skelton A19;' 'Skelton A16;' and 'Skelton X78.
Figure 6:
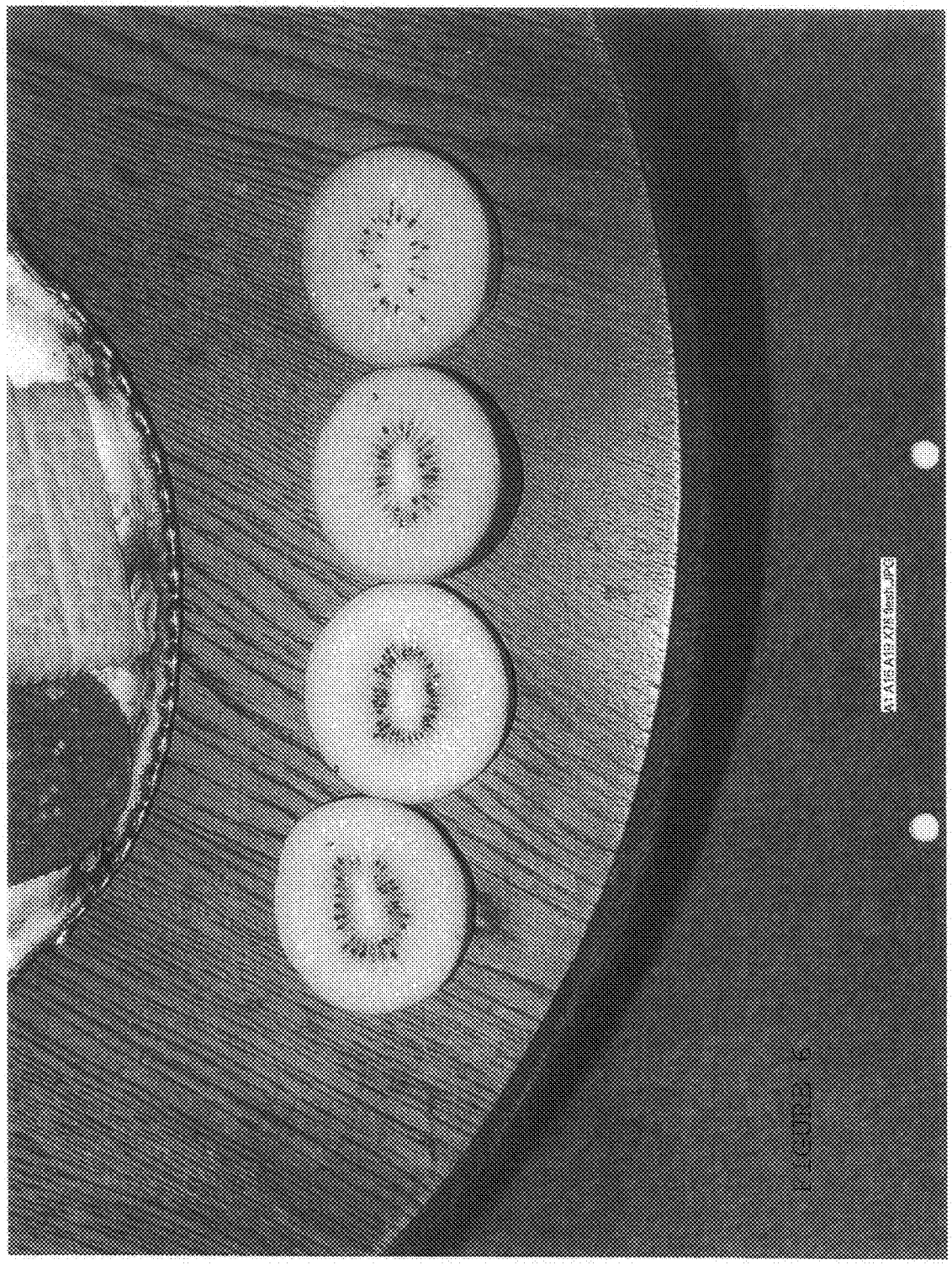
' and FIG. 6 shows typical fruit of the new variety in the studio compared with other varieties in cross-section, in order: 'A1;' 'Skelton A16;' 'Skelton A19;' and 'Skelton X78.'

The distinctive characteristics of 'Skelton A19' were first observed with the first fruit maturing in April 1999. The distinctive characteristics of this new Kiwi variety, described in detail below and shown in the accompanying photographs, were observed in April 2006 at Rangiriri, New Zealand. The age of the plants was approximately seven years from grafting onto seedling rootstocks.

Comparison with the similar variety 'HORT16A' (U.S. Plant Pat. No. 11,066) shows that 'Skelton A19' may be distinguished as follows in Table 1:

TABLE 1

Comparison With Similar Variety.
Observations made under New Zealand Growing Conditions

| Characteristic | HORT16A | A19 |
|---|---|---|
| FRUIT | | |
| Harvest Date | Early May | Early April |
| Color of Ripe Pericarp | Medium yellow (12C/12B) | Yellow (3B) |
| Skin Color | Yellow-brown 199B | Yellow-brown 199B |
| Mean Fresh Weight | 43-176 grams | 95-105 grams |
| Mean Dry Matter at Harvest | 18% | 14.5-17.5% |
| Average Length | 79.1 mm | 70.0 mm |
| Average Width | 51.1 mm | 46.0 mm |
| Core Diameter | 12.4 mm | 16.5 mm |
| Width/Length Ratio | 0.65 | 0.61 |
| Sweetness (Brix) at maturity for consumption | 15.6% | 16.5% |
| General Shape | Ovoid | Obovoid |
| Cross sectional shape | Circular | Circular |
| Shape at Stylar End | Strongly blunt protruding | Slightly blunt protruding |
| Skin: Hairiness | Present | Low/downy |
| VINE | | |
| Shoots: | | |
| Color | 144B | 144C |
| Texture | Smooth | Smooth |
| Stem: | | |
| Colour-upper | 177A | 166A |
| Colour-lower | 199A | 199A |
| Mean diameter | 9.5 mm | 9.5 mm |
| Texture | Smooth | Smooth |
| Lenticel (if present) | Present | Present |
| LEAF: | | |
| Colour-upper | 147A | 138A |
| Colour-lower | 148B | 138C |
| Shape | Orbiculate | Broadly Orbiculate |
| Length | 124 mm | 114.1 ± 15.7 mm |
| Width | 151 mm | 128.8 ± 20.5 mm |
| Apex | Acute | Retruse |
| Base | Cordate | Cordate |
| Margin | Ciliate | Ciliate |
| Texture | Glabrous | Glabrous |
| FLOWER | | |
| Inflorescence: | | |
| Predominant number of flowers | 3 | 3 |

TABLE 1-continued

Comparison With Similar Variety.
Observations made under New Zealand Growing Conditions

| Characteristic | HORT16A | A19 |
|---|---|---|
| Petiole: | | |
| Length | 103 mm | 42.9 ± 8.1 mm |
| Colour | 145B | 146C |
| Pedicel: | | |
| Length | 27.1 mm | 34.0 ± 7.0 mm |
| Colour | 151A | 145A |
| Hairs | Present | Present |
| Length of hairs | Very short | Very short |
| Flower: | | |
| Coloration of petals | Bi-coloured | Bi-coloured |
| Primary Colour | White 155B | White 155C |
| Secondary colour base of petal | Green 144D | Green 144C |
| Diameter | 51 mm | 42.9 ± 2.9 mm |
| Arrangement of Petals | Overlapping | Overlapping |
| Mean number of petals/flower | 6 | 6-7 |
| Mean length of petals | 28.8 mm | 20.2 ± 1.3 mm |
| Mean width of petals | 23.9 mm | 14.8 ± 1.8 mm |
| Petal ratio of length to width | 1.21 | 1.36 |
| Petal shoulder | Present | Present |
| Filament colour | Green/White 157A | Green/White 157B |
| Anther colour | Yellow 16C | Burnt orange 17B |
| Attitude of styles | Semi erect | Semi erect |
| Curvature of styles | Absent | Absent |
| Colour of styles | White 155D | White 155C |
| Amount of hair on ovary | Dense | Dense |
| Colour of ovary | White 157B | White Green 157C |
| Number of sepals | 6-7 | 6-7 |
| Colour of sepal | Green 148D | Green with orange brown margin 148C |
| Length of sepals | | |
| Range | 8.7-12.4 mm | 5.9-8.0 mm |
| Mean | 11.4 mm | 6.8 ± 0.6 mm |
| Sepal diameter | 9.1 mm | 4.7 ± 0.6 mm |
| Flower Opening | Mid October | Early October |
| Vegetative bud break | Early September | Early September |
| Plant/fruit disease & pest resistance | None | None |
| Plant hardiness zone or heat/cold resistance | Not Known | Not known |

Color references are in accord with the R.H.S. Colour Chart, the Royal Horticultural Society, London, 2001

The most striking difference between 'Skelton A19' and 'HORT16A' is that of fruit shape, flowering and harvest times. 'Skelton A19' obovoid fruit have slightly blunt protruding stylar end, whereas 'HORT16A' are ovoid with a strongly protruding blunt stylar end. In addition the flowering and harvest dates of 'Skelton A19' are approximately two weeks prior to that of 'HORT16A' in early October and early April, respectively.

The embodiments of the invention in which an exclusive property or privilege is claimed are defined as follows:

1. A new and distinct kiwi plant of the species *A. chinensis* substantially as herein described and illustrated.

* * * * *

2007-0104-0051

31 2/3 x 15 x 7/8 (cm)